United States Patent [19]
Mohr et al.

[11] Patent Number: 4,900,149
[45] Date of Patent: Feb. 13, 1990

[54] METHOD FOR THE SIMULTANEOUS ANALYSIS OF SEVERAL ELEMENTS

[75] Inventors: Joachim Mohr, Jena; Holger Gerecke, Oebisfelde, both of German Democratic Rep.

[73] Assignee: Jenoptik Jena G.m.b.H., Jena, German Democratic Rep.

[21] Appl. No.: 215,015

[22] Filed: Jul. 5, 1988

[30] Foreign Application Priority Data

Sep. 7, 1987 [DD] German Democratic Rep. ... 306719

[51] Int. Cl.$^4$ ................................................ G07J 3/30
[52] U.S. Cl. ..................................... 356/311; 356/312
[58] Field of Search ..................... 356/311, 312, 314; 313/209

[56] References Cited

U.S. PATENT DOCUMENTS 4,318,614  3/1982  Falk et al. ........................... 356/311

Primary Examiner—Léon Scott, Jr.
Attorney, Agent, or Firm—Jordan and Hamburg

[57] ABSTRACT

A method for the simultaneous analysis of several elements, in which the analyte, after a thermal vaporization, is athermally excited in the same volume by a hollow cathode discharge, assigns a discharge pressure range, in which the atomization temperature increases steadily with pressure, to the "cold" and "hot" hollow cathode discharge. The transition from one range to the other takes place suddenly. The discharge current intensity is increased with increasing atomization temperature.

2 Claims, 3 Drawing Sheets

METHOD FOR THE SIMULTANEOUS ANALYSIS OF SEVERAL ELEMENTS

FIELD OF THE INVENTION

The invention is directed to a method for the simultaneous analysis of several elements, in which an analyte, after thermal vaporization, is excited athermally in the same volume by a hollow cathode discharge.

BACKGROUND OF THE INVENTION

As disclosed in German Offenlegungsschrift No. 3,600,943, it has previously been customary to optimize and keep constant the discharge pressure and the discharge current intensity matched to the element to be detected, during the atomization and excitation steps of the analytical cycle. This method is permissible for the simultaneous analysis of several elements if the atomization of the analyte components are to start or proceed to completion at approximately the same temperature. Such elements are, for example, Mn, Cr, Fe, Co. A different group is formed by Cd, Zn, Pb, Au, Ag. If analytes containing elements from both groups or even other elements are to be analyzed, a satisfactory analytical result for all the elements to be detected cannot be obtained by keeping the parameters of discharge pressure and discharge current intensity constant within the same analytical cycle.

SUMMARY OF THE INVENTION

It is an object of the invention to increase the detectability and the reproducibility for a larger number of elements detectable in one analytical cycle.

The object of the invention is furthermore to excite elements with mutually different atomization and excitation conditions to radiate adequately in one analytical cycle for an acceptable analysis signal. equately in one analytical cycle for an acceptable analysis signal.

Pursuant to the invention, the above objects are achieved by a method for the simultaneous analysis of several elements, in which the analyte, after a thermal vaporization, is excited athermally in the same volume by a hollow cathode discharge and the athermal excitation of the elements to be detected is divided essentially into two segments and determined by discharge conditions. Each of the two segments is assigned discharge pressure ranges in which the pressure rises steadily with the atomization temperature and the transition from the one to the other range takes place suddenly with a pressure-change rate of at least 40 Pa/°K. It is advantageous if the discharge current intensity in both segments as well as in the transition from one to the other experiences an essentially constant increase with increasing atomization temperature.

BRIEF FIGURE DESCRIPTION

The invention will be described below in greater detail by means of the accompanying drawings, wherein.

DETAILED DISCLOSURE OF THE INVENTION

Figure 1:
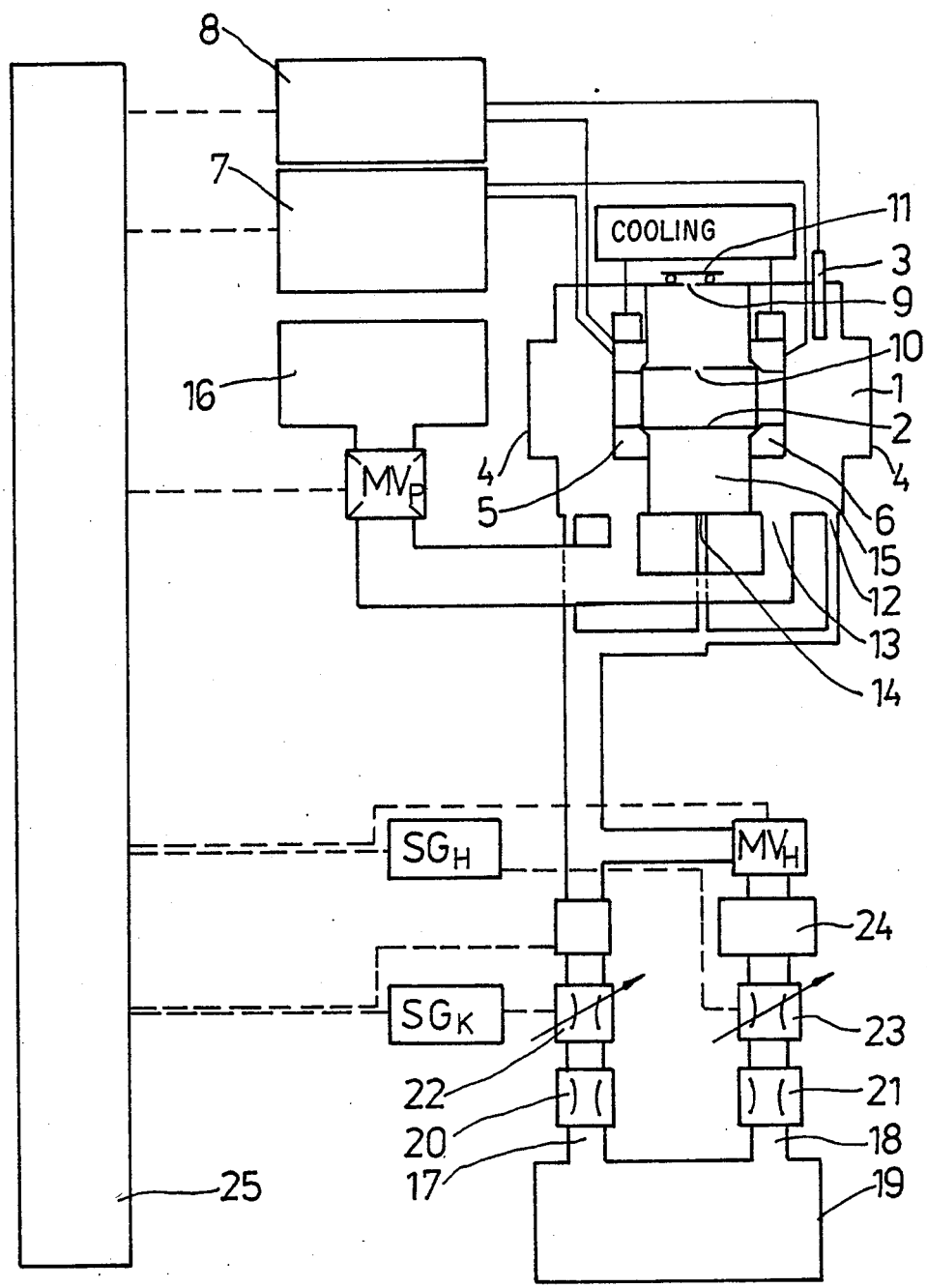
FIG. 1 shows an arrangement in accordance with the invention.

The arrangement shown in FIG. 1 comprises an externally supplied FANES (Furnace Atomic Nonthermal Excitation Spectrometry) measuring head, which contains a vaporization tube 2 and at least one anode 3 in a discharge vessel 1 and the faces of which are closed off by a window 4. The vaporization tube 2, held in water-cooled electrodes 5, 6, is connected with a source of heating current 7 and also as cathode, just as the anode 2, connected with a supply system to the hollow cathode discharge 8. At least 9 of pipette openings 9, 10 can be closed off by a lid 11. A gas supply channel 12 and a gas discharge channel 13 are provided in the vicinity of the faces of the vaporization tube 2. At least one gas supply channel 14 discharges into the space 15 surrounding the vaporization tube 2. While the gas discharge channels 13 are connected over a magnetic valve $MV_P$ with a pump 16, the gas supply channels 12 and 14 are connected over two mutually separate supply sections 17, 18 with a gas supply 19. Each of the sections 17, 18 has a gas pressure reducing valve 20, 21 and an adjustable needle valve 22, 23. In section 17, the outlet side of the needle valve 22 is connected directly to a magnetic valve $MV_K$. In section 18, a gas cylinder 24 is connected between the needle valve 23 and a magnetic valve $MV_H$. The needle valve 22 is coupled with the control element $SG_K$, the needle valve 23 with the control element $SG_H$ and both control elements, as well as the magnetic valves $MV_K$ and $MV_H$ are connected with a control unit 25. The control unit 25 moreover is coupled with the supply system 8 of the hollow cathode discharge, with the heating current source 7 and with the magnetic valve $MV_p$.

Figure 3:
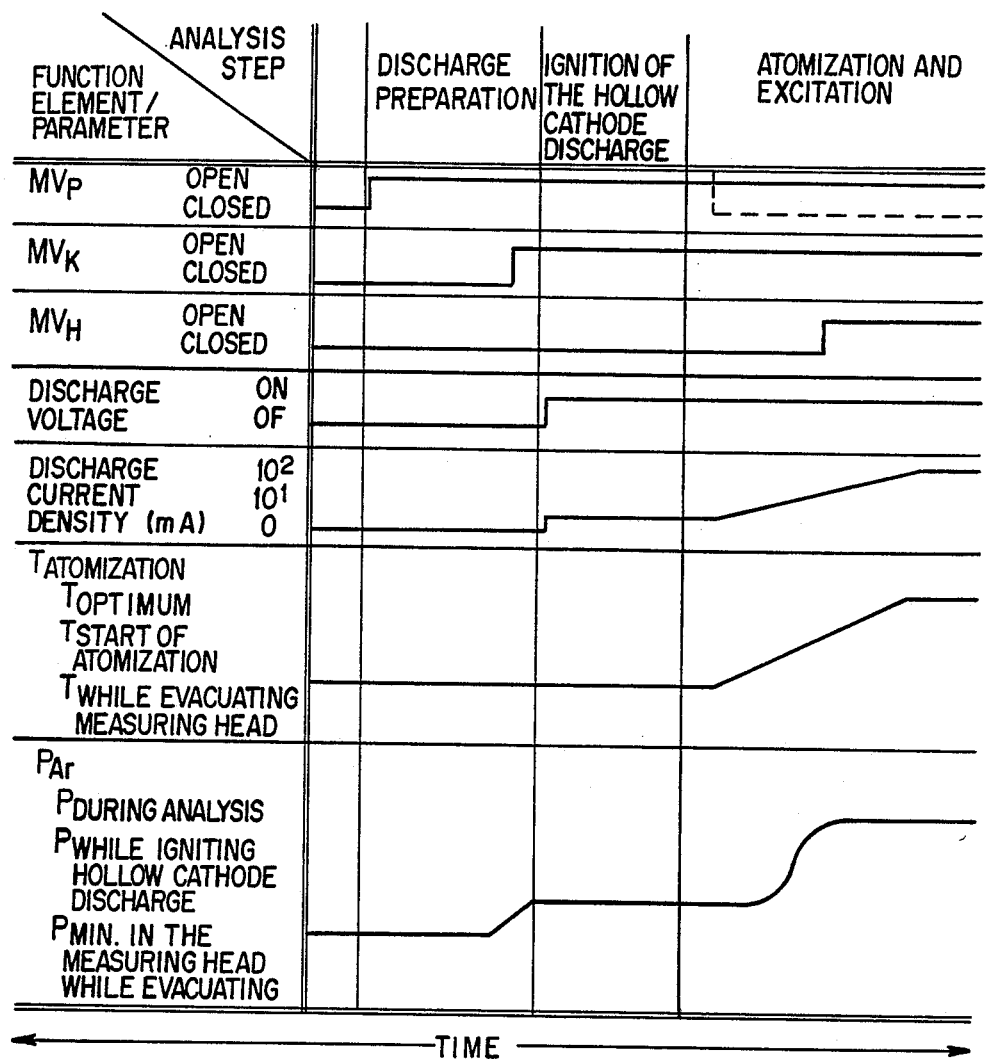
FIG. 3 is a time sequence schedule table.

After a thermal pretreatment of the sample in a drying step and an ashing step, the discharge preparation and the atomization and excitation of the analyte to be examined follow. The temperature $T_{At}$ of the vaporization tube 2 is controlled via control unit 25 as RAMP progression, the discharge current intensity $I_{HKE}$ is controlled as a function $F_1$ of the atomization temperature $T_{At}$ and the discharge gas pressure is controlled as a function of $F_{2K}$ or $F_{2H}$ of $T_{At}$. $F_{2K}$ describes the course of the pressure during the so-called "cold" hollow cathode discharge, which extends as a first section up to the start of the "hot" hollow cathode discharge, at which an intensified thermal electron emission sets in. $F_{2H}$ is descriptive for the second section. The control of the function elements and the change in the parameters during the atomization and excitation phases is made clear in the time sequence schedule shown in FIG. 3. The following is a key for the symbols:

$T_{evak}$ = temperature while evacuating measuring head
$T_{app}$ = appearance temperature (start of the atomization)
$T_{opt}$ = optimum atomization temperature
$P_{Ar}$ = argon gas pressure
$P_{Anal}$ = gas pressure during analysis
$P_{zund}$ = gas pressure while igniting the hollow cathode discharge
$P_{evak}$ = minimum pressure in the measuring head while evacuating
HKE = hollow cathode discharge The broken line for the function of the magnetic valve $MV_p$ illustrates a possible pump stop during the atomization and excitation.

Figure 2:
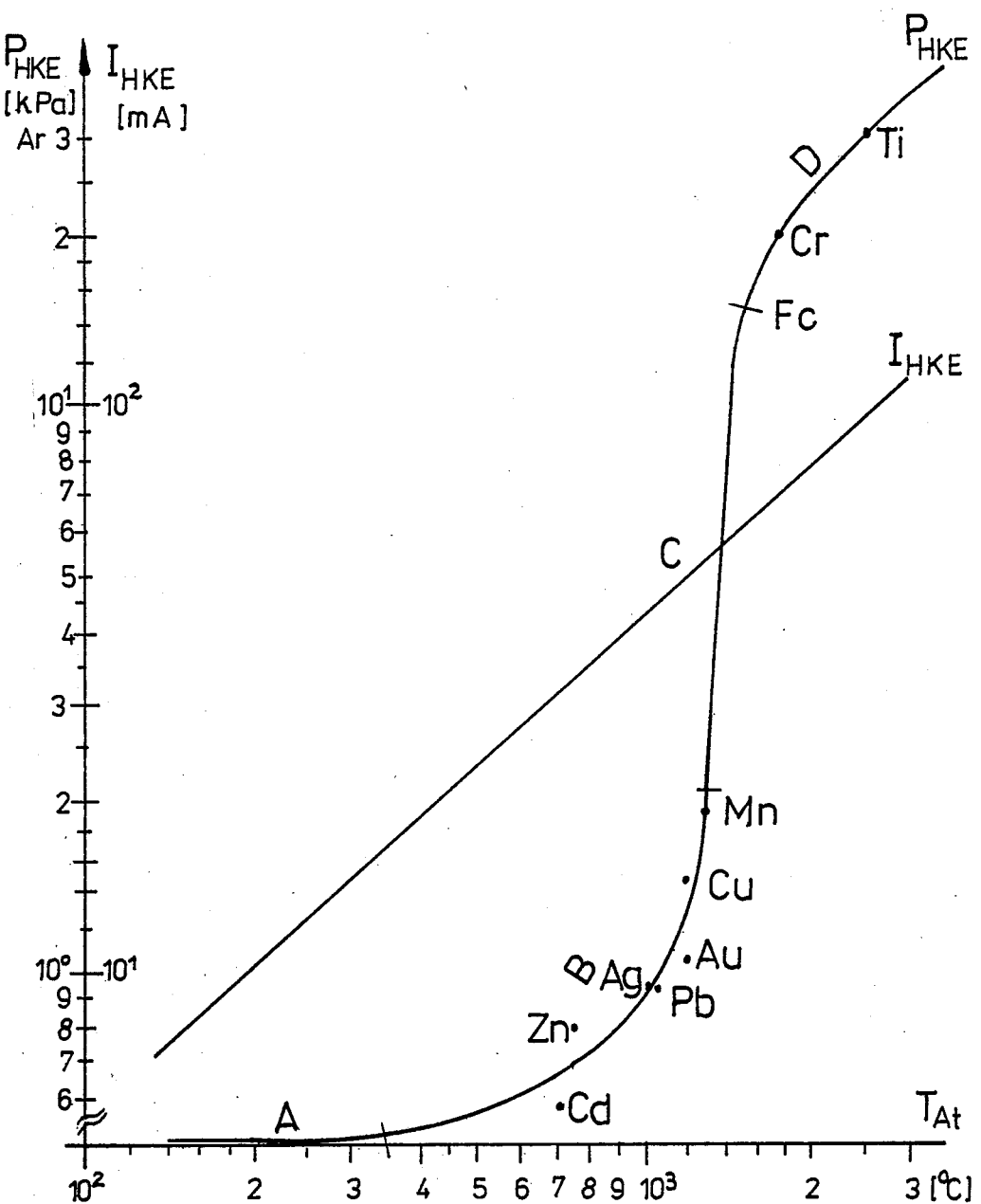
FIG. 2 shows the discharge pressure and the discharge current intensity as a function of the temperature of the vaporization tube.

The course of the discharge pressure, shown in FIG. 2, is produced with the controlled function of the magnetic valves $MV_p$, $MV_K$ and $MV_H$. The discharge current intensity $I_{HKE}$, generated in the supply system for the hollow cathode discharge 8, is controlled by the control unit.

While the discharge current density increases essentially constantly, the course of the discharge pressure $P_{HKE}$ after a Section A (ignition of the hollow cathode discharge) is arranged in Sections B, C and D. The "cold" hollow cathode discharge is assigned to Section B, the "hot" hollow cathode discharge to Section D. C represents a transition area, in which a steep, sudden increase in pressure of at least 40 Pa/°K. is necessary. The gas tank 24 in section 18 serves to rapidly attain the pressure level of the "hot" hollow cathode discharge.

the curve shown in one in which argon is the discharge gas and the pressure is measured at the pipetting opening 9.

The described method of changing the discharge pressure and the discharge charge current intensity with the atomization temperature for the radiation induced excitation of a plurality of elements in one analytical cycle is, of course, not bound uniquely to the arrangement described.

We claim:

1. In a method for the simultaneous analysis of several elements, in which an analyte, after thermal vaporization, is excited in the same volume athermally by a hollow cathode discharge and the athermal excitation of the elements to be detected, which is essentially divided into two sections, is determined, the improvement comprising assigning the discharge pressure ranges, in which the pressure increases steadily with the atomization temperature, to each of the two sections, and providing a transition from one range to the other suddenly with a pressure change rate of at least 40 Pa/°K.

2. The method of claim 1, wherein, aside from the discharge pressure change with increasing atomization temperature, there is an essentially constant increase in the discharge current intensity in both sections, as well as in the transition from the one to the other.

* * * * *